US007767710B2

(12) United States Patent
Waddell

(10) Patent No.: US 7,767,710 B2
(45) Date of Patent: *Aug. 3, 2010

(54) METHOD FOR TREATING OSTEOARTHRITIS

(75) Inventor: David D. Waddell, Shreveport, LA (US)

(73) Assignee: Calosyn Pharma, Inc., Sharon, MA (US)

( * ) Notice: Subject to any disclaimer, the term of this patent is extended or adjusted under 35 U.S.C. 154(b) by 1434 days.

This patent is subject to a terminal disclaimer.

(21) Appl. No.: 11/138,744

(22) Filed: May 25, 2005

(65) Prior Publication Data

US 2006/0270716 A1 Nov. 30, 2006

(51) Int. Cl.
- A61K 31/00 (2006.01)
- A61K 31/44 (2006.01)
- A61K 31/275 (2006.01)
- A61K 31/135 (2006.01)
- A01N 37/34 (2006.01)
- A01N 33/02 (2006.01)

(52) U.S. Cl. .................. 514/523; 514/211.07; 514/356; 514/646; 514/654; 514/825

(58) Field of Classification Search ............ 514/211.07, 514/356, 523, 646, 654, 825
See application file for complete search history.

(56) References Cited

U.S. PATENT DOCUMENTS

| | | | |
|---|---|---|---|
| 5,478,848 | A | 12/1995 | Aune |
| 5,811,449 | A | 9/1998 | Medford et al. |
| 6,100,258 | A | 8/2000 | Breault |
| 6,147,250 | A | 11/2000 | Somers |
| 6,190,691 | B1 | 2/2001 | Mak |
| 6,197,801 | B1 | 3/2001 | Lin |
| 6,221,861 | B1 | 4/2001 | Seegmiller |
| 6,239,182 | B1 | 5/2001 | Zaneveld et al. |
| 6,337,325 | B1 | 1/2002 | Schonharting et al. |
| 6,365,603 | B1 | 4/2002 | Breault |
| 6,416,758 | B1 | 7/2002 | Thorpe et al. |
| 6,521,615 | B2 | 2/2003 | Seegmiller |
| 6,548,699 | B1 | 4/2003 | Somers |
| 6,861,429 | B2 | 3/2005 | Beswick et al. |
| 6,924,273 | B2 | 8/2005 | Pierce |
| 6,979,685 | B1 | 12/2005 | Beatch et al. |
| 7,067,144 | B2 | 6/2006 | Demopulos et al. |
| 2001/0009910 | A1 | 7/2001 | Seegmiller |
| 2002/0065266 | A1 | 5/2002 | Jensen et al. |
| 2002/0068718 | A1 | 6/2002 | Pierce |
| 2002/0107193 | A1 | 8/2002 | Glazner |
| 2004/0087642 | A1 | 5/2004 | Zeldis et al. |
| 2004/0167117 | A1 | 8/2004 | Adams et al. |
| 2004/0229802 | A1 | 11/2004 | Fleiszig et al. |
| 2005/0014748 | A1 | 1/2005 | Pajouhesh et al. |
| 2005/0063913 | A1 | 3/2005 | Pruitt et al. |
| 2005/0090553 | A1 | 4/2005 | Shapiro |
| 2005/0152905 | A1 | 7/2005 | Omoigui |
| 2005/0182022 | A1 | 8/2005 | Pierce |
| 2005/0182083 | A1 | 8/2005 | Weinstein et al. |
| 2006/0269579 | A1 | 11/2006 | Waddell |
| 2006/0270716 | A1 | 11/2006 | Waddell |

FOREIGN PATENT DOCUMENTS

| | | |
|---|---|---|
| WO | WO-02/49603 | 6/2002 |
| WO | WO/2005/013947 | 2/2005 |
| WO | WO/2005/025293 | 3/2005 |

OTHER PUBLICATIONS

Galer et al. 2004, Topical lidocain patch 5% may target a novel underlying pain mechanism in osteoarthritis. Current Medical Research and Opinion, vol. 20 No. 9, pp. 1455-1458.*
*Osteoarthritis*, National Institute of Arthritis and Musculoskeletal and Skin Diseases, National Institutes of Health, NIH Publication No. 02-4617, Jul. 2002.
*Rheumatoid Arthritis*, National Institute if Arthritis and Musculoskeletal and Skin Diseases, National Institutes of Health, NIH Publication No. 04-4179, May 2002.
Biochemistry and Metabolism of Articular Cartilage in Osteoarthritis, H. J. Mankin and K.D. Grant, *Osteoarthritis: Diagnosis and Medical/Surgical Management*, $2^{nd\ Ed.}$, Philadelphia 1992.
Wohlrab et al., "Influence of Ion Channels on the Proliferation of Human Chondrocytes", Biorheology 39, pp. 55-61, 2002.
Boileu, Christelle, et al., "Oral Treatment with PD-0200347, an $\alpha_2\delta$ Ligand, Reduces the Development of Experimental Osteoarthritis by Inhibiting Metalloproteinases and Inducible Nitric Oxide Synthase Gene Expression and Synthesis in Cartilage Chondrocytes," Arthritis & Rheumatism, vol. 52, No. 2, Feb. 2005, pp. 488-500.
Bellamy, N., "The WOMAC Knee and Hip Osteorthritis Indices: Development, validation, globalization and influence on the development of the AUSCAN Hand Osteoarthritis Indices," Clin. Exp. Rheumatol 2005; 23 (Suppl. 39); 148-153.
Guidance for Industry Clinical Development Programs for Drugs, Devices, and Biological Products Intended for the Treatment of Osteoarthritis (OA), U.S. Department of Health and Human Services, Food and Drug Administation, Jul. 1999.
Osteoarthritis (OA): Joint Disorders: Merck Manual Professional, Section: Musculoskeletal and Connective Tissue Disorders, Subject: Joint Disorders, http://www.merck.com/mmpe/print/sec04/ch034/ch034e.html. Downloaded May 22, 2009.
Rheumatoid Arthritis (RA): Joint Disorders: Merck Manual Professional, Section: Musculoskeletal and Connective Tissue Disorders, Subject: Joint Disorders, http://www.merck.com/mmpe/print/sec04/ch034/ch034b.html. Downloaded May 22, 2009.
Kolomytkin, Oleg V., et al., "*IL-1β-induced Production of Metalloproteinases by Synovial Cells Depends on Gap Junction Conductance*," Am J Physiol Cell Physiol 282: C1254-C1260, 2002.
Waddell, David D., MD., et al., "*Gap Junctions in Osteoarthritis*,", Department of Orthopaedic Surgery, LSU Health Sciences Center—Shreveport and Department of Anatomy, Oklahoma State University College of Osteopathic Medicine, Feb. 17, 2002.

* cited by examiner

*Primary Examiner*—Sreeni Padmanabhan
*Assistant Examiner*—Kara R McMillian
(74) *Attorney, Agent, or Firm*—Goodwin Procter LLP

(57) ABSTRACT

A method and composition for treating osteoarthritis with ion-channel regulators is disclosed. The ion-channel regulators are used alone or in combination with other osteoarthritis treatment agents, including but not limited to injectable agents such as viscosupplements and steroids. A composition comprising one or more ion-channel regulator(s) and one or more osteoarthritis treatment agent(s) is also disclosed.

6 Claims, No Drawings

METHOD FOR TREATING OSTEOARTHRITIS

BACKGROUND OF THE INVENTION

1. Field of the Invention

The present invention relates to the treatment of pain and inflammation in body tissues. In particular, the present invention relates to methods and compositions for treating osteoarthritis using ion-channel regulators.

2. Discussion of the Background

Osteoarthritis is a degenerative joint disease in which cartilage and bone are primarily affected. Osteoarthritis is especially common among older people, and usually affects a joint on one side of the body. In osteoarthritis, the cartilage breaks down and wears away, causing pain, swelling, and loss of motion of the joint. Further details are provided in *Osteoarthritis*, National Institute of Arthritis and Musculoskeletal and Skin Diseases, National Institutes of Health, NIH Publication No. 02-4617, July, 2002 which is incorporated herein by reference.

Rheumatoid arthritis is a systemic disease which, when manifested in joints, primarily affects the synovial membrane. Rheumatoid arthritis begins at a younger age than osteoarthritis, is usually present bilaterally in the joints, and sometimes results in feelings of sickness, tiredness, and fever. Further details are provided in *Rheumatoid Arthritis*, National Institute of Arthritis and Musculoskeletal and Skin Diseases, National Institutes of Health, NIH Publication No. 04-4179, May, 2004 which is incorporated herein by reference.

Inflammation is a fundamental biological process consisting of a dynamic complex of cytologic and chemical reactions that occur in the affected blood vessels and adjacent tissues in response to an injury or abnormal stimulation caused by a physical, chemical, or biological agent. The process of inflammation includes: 1) local tissue reactions and resulting morphologic changes; 2) destruction or removal of injurious material; and 3) responses that lead to repair and healing. The so-called "cardinal signs" of inflammation are redness, heat (or warmth), swelling, pain and inhibited or lost function. All of these signs may be observed in certain instances, but no one of them is necessarily always present. A disease that involves inflammation is herein referred to as an "inflammatory disease".

The proteins known as cytokines are important factors in the onset and maintenance of inflammation. Cytokines, which are produced by synovial lining cells, cartilage cells, as well as by other types of cells, regulate numerous biological responses, including cell growth, and the nature and extent of proteins that are made by cells. Cytokines include interferons (IFNs), colony stimulating factors (CSFs), interleukins (ILs), and tumor necrosis factors (TNFs). It is known that the presence of inflammatory cytokines (IL-1, IL-8, TNF) initiates a series of complex cellular and molecular events, including the expression of adhesion molecules, the production of secondary inflammatory mediators (prostaglandins, leukotrienes), and the production of growth factors.

Arthritis is an inflammatory disease characterized by inflammation of a joint, which term includes synovial tissue and membranes. There are many forms of arthritis, including without limitation, osteoarthritis (hypertrophic or degenerative arthritis), rheumatoid arthritis, arthritis due to infection (tuberculosis, Lyme disease, rheumatic fever, etc.), suppurative arthritis, juvenile arthritis, and gouty arthritis. Elevated tissue levels of IL-1, IL-8, and TNF are found in arthritis and in other inflammatory conditions.

In osteoarthritis, the cartilage that covers the ends of the bones that form the joint is slowly degraded by the action of various enzymes, particularly the matrix metalloproteinases (MMPs) which are secreted into the synovial fluid of the joint by the synovial lining cells in response to stimulation by various proinflammatory cytokines, particularly IL-1 and TNF. The destruction of cartilage by the MMPs perpetuates the inflammatory reaction and leads to the joint pain associated with osteoarthritis. Further details are provided in "Biochemistry and Metabolism of Articular Cartilage in Osteoarthritis", H. J. Mankin and K. D. Brant, in *Osteoarthritis: Diagnosis and Medical/Surgical Management*, $2^{nd}$ Ed., R. W. Moskowitz, D. S. Howell, V. M. Goldberg, and H. J. Mankin, W.B. Saunders Co., Philadelphia (1992), which is incorporated herein by reference.

Ion channels are glycoprotein structures located in the membrane of cells, including synovial cells and cartilage cells, which allow ions, particularly monovalent and divalent cations and anions, to pass through the membrane. Ion channels include but are not limited to calcium-ion channels, sodium-ion channels, potassium-ion channels, chloride-ion channels, cation-ion channels, anion-ion channels, connexon channels and non-selective ion channels.

Ion-channel regulators are a known group of agents, usually chemical in nature, that alter the entry of certain ions into or out of cells and cellular organelles, depending on whether the intracellular or extracellular concentration of the particular ion is greater, and on the electrical potential difference that exists between the inside and the outside of the cell. The combined effect of the concentration difference and the electrical potential difference is called the electrochemical gradient. When the gate of an ion channel is open, the ions will flow down their electrochemical gradient unless they are prevented from doing so as, for example, by means of a chemical ion-channel regulator. Ion-channel regulators that cause a reduction in the ion flow that would otherwise occur are referred to as "ion-channel blockers." Ion-channel regulators that cause an increase in the ion flow that would otherwise occur are referred to as "ion-channel activators."

Ion-channel regulators are commonly used for treating a variety of conditions, including cardiac conditions such as atrial fibrillation, supraventricular tachycardias, hypertrophic cardiomyopathy and hypertension, as well as migraine headaches, the prevention of brain damage, and other disorders. Certain ion-channel regulators and related compounds have been described in the art as being useful in the treatment of inflammatory diseases. For example, Thorpe et al. (U.S. Pat. No. 6,416,758) disclose antibody conjugate kits for selectively inhibiting VEGF binding to only one (VEGFR2) of the two VEGF receptors. The antibodies inhibit angiogenesis and induce tumor regression, and can be used for treatment of all conditions where angiogenesis is a factor (including arthritis). Thorpe, et al. mention CAI, an angiogenesis inhibitor that acts as a calcium-channel regulator that prevents actin reorganization, endothelial cell migration and spreading on collagen IV.

Stamler, et al. (U.S. Pat. No. 6,359,182) disclose C nitroso compounds derived from a wide variety of drugs, including known calcium channel regulators (verapamil, diltiazem, etc.). These derivatives provide relaxation and platelet inhibiting effects, and due to their NO donor function, are said to be useful for treating arthritis.

Schonharting, et al. (U.S. Pat. No. 6,337,325) provide a combination preparation which includes a compound having a phosphodiesterase inhibiting action, and a compound which reduces the biologically effective intracellular Ca2+ content (such as verapamil). Their preparation can be used to treat rheumatoid arthritis.

Medford, et al. (U.S. Pat. No. 5,811,449) disclose a method for treatment of atherosclerosis and other cardiovascular and inflammatory diseases that are mediated by VCAM 1 ("vascular cell adhesion molecule 1"). The list of diseases includes rheumatoid arthritis and osteoarthritis. The dithiocarboxylates and other compounds used with the method can be attached to a large number of pharmaceutically-active compounds, including calcium-channel regulators (verapamil, diltiazem, nifedipine).

Certain known compositions for the relief of pain associated with inflammatory disease states may contain ion-channel regulators and related compounds. For example, Breault (U.S. Pat. Nos. 6,365,603 and 6,100,258) describes aromatic/phenyl compounds useful for inhibiting the pain enhancing effects of E-type prostaglandins. The compounds can be used to treat pain associated with rheumatoid arthritis, osteoarthritis, and osteoporosis, and may contain additional agents such as calcium-channel regulators.

Mak (U.S. Pat. No. 6,190,691) provides methods for treating several inflammatory conditions that are mediated by TNF production (including rheumatoid arthritis). Treatment is accomplished by administering a therapeutically effective amount of any of a number of compounds, including calcium-channel regulators such as verapamil, nicardipine or isradipine. Mak teaches direct injection of large amounts of (+)-verapamil (20-40 mg in a 10 mg/mL solution) into joints for the treatment of rheumatoid arthritis.

There is no known cure for osteoarthritis, and consequently clinical efforts aimed at treating it are presently directed toward symptomatic relief of pain. Conventional therapies include treatment with analgesics or non-steroidal anti-inflammatory drugs (aspirin, ibuprofen, naproxen, COX 2 inhibitors such as CELEBREX and VIOXX, and the like), interarticular injection of corticosteroids and unmodified or modified hyaluronan (a treatment called viscosupplementation), as well as the use of steroids, antibiotics, glucosamine, chondroitin, immunomodulators, and penicillamine. Traditional remedies such as the application of heat for temporary, local pain relief are helpful for some patients, and suitable exercise and physical therapy programs can help in maintaining joint mobility. Joint replacement surgery may be advised in severe cases.

Despite the availability of a wide range of medications and treatment modalities for arthritis and inflammatory diseases in general, as described above, none has proved to be entirely satisfactory for osteoarthritis. In particular, there remains a need for innovative treatments that target the underlying cause of osteoarthritis, for example the production of MMPs, and thereby help reduce, eliminate, or slow its progression (expressed symptomatically by bone erosion, cartilage erosion, inflammation, swelling, abnormal neovascularization, etc.).

BRIEF SUMMARY OF THE INVENTION

According to its major aspects and broadly stated, the present invention provides a method and compositions for treating the pain, inflammation and loss of function associated with osteoarthritis, by using certain agents that are capable of regulating the movement of ions in and out of cells through structures embedded in the cell membrane called ion channels. As briefly described above, such agents are referred to herein as "ion-channel regulators".

One embodiment of the present invention comprises a method for treating osteoarthritis, which comprises directly administering to the affected joint, preferably by direct injection into the closed cavity of the joint ("intraarticular injection"), a therapeutically effective amount of at least one ion-channel regulator, alone or in combination with at least one other osteoarthritis treatment agent.

The method of the present invention treats the underlying cellular processes that lead directly to the pain and tissue destruction associated with osteoarthritis. In one embodiment, the invention comprises administering to the synovial tissue an effective amount of ion-channel regulator; i.e., an amount that is sufficient to reduce any or all of the symptoms of osteoarthritis without producing any of the undesirable side effects resulting from an overdose of ion-channel regulator, such as tissue death or injury, joint swelling, etc. The present invention provides a means for interfering with cell signaling by the cytokine IL-1, the major inflammatory cytokine associated with osteoarthritis, thereby leading to lower MMP levels and correspondingly lower cartilage destruction and resultant pain. It is believed that this method does not necessarily affect the production of IL-1, but rather alters its consequences by interfering with the synthesis of MMPs at a point subsequent to the binding of IL-1 to its receptor on the surface of the cells, which is known to those skilled in the art as being the first step in the synthesis process. This method is contrasted with the use of certain ion-channel regulators as a means of interfering with the production of the cytokine TNF, e.g. in the treatment of the systemic inflammatory disease rheumatoid arthritis (see Mak, supra).

Ion-channel regulators contemplated as being useful in the present invention include, but are not limited to, calcium-channel regulators, sodium-channel regulators, potassium-channel regulators, chloride-channel regulators, cation-ion channel regulators, anion-ion channel regulators, non-selective ion channel regulators and connexon-channel regulators (i.e., chemical agents that regulate the movement of ions and molecules through connexons in synovial cells, which consist of the protein known as connexin 43).

A preferred method of administering the ion-channel regulator is to directly inject a pharmaceutically acceptable composition containing at least one ion-channel regulator into the closed cavity of an arthritic joint. The ion-channel regulator may be administered alone or in combination with other medicaments, preferably other chemical agents used to treat osteoarthritis (herein referred to as "osteoarthritis treatment agents"). Osteoarthritis treatment agents include, but are not limited to pharmaceutically acceptable viscosupplements, steroidal and non-steroidal anti-inflammatory agents, glucosamines, chondroitins, and so forth.

In another embodiment, the present invention comprises a novel composition useful for treating osteoarthritis in accordance with the present invention. The composition of the invention comprises at least one ion-channel regulator and at least one other osteoarthritis treatment agent. In one preferred embodiment, a composition comprises at least one ion-channel regulator and at least one injectable osteoarthritis treatment agent, most preferably a viscosupplement. The compositions of the invention may also contain other materials such as fillers, stabilizers, coatings, colorizing and flavoring agents, preservatives, fragrances, and other additives known in the art.

In its various embodiments, the present invention provides several treatment modalities to users. Treatment may consist of the administration of an effective amount of at least one ion-channel regulator, preferably in a pharmaceutically acceptable composition that contains at least one such compound. Alternatively, treatment may include administration of at least one ion-channel regulator in combination with administration of at least one other osteoarthritis treatment agent, preferably in a composition containing both the ion-channel regulator and the other osteoarthritis treatment agent. The treatment can readily be customized to the individual patient's needs, and may be used instead of or in conjunction with other treatment modalities including, but not limited to, physical therapy, treatments that provide localized pain relief (heat, massage, application of liniments, etc.), and other medications that help reduce disability, relieve pain, and improve the patient's quality of life.

Other features and advantages of the present invention will be apparent to those skilled in the art from a careful reading of the Detailed Description of the Invention presented below.

DETAILED DESCRIPTION OF THE INVENTION

The present invention provides methods and compositions wherein ion-channel regulators are used to treat the inflammation, pain and tissue destruction associated with osteoarthritis.

Without intending to be bound by theory, it is believed that the presence of inflammatory cytokines in the joint leads to the entry and exit of certain cellular ions, e.g. calcium, sodium, potassium, chloride ions, etc., into and out of cells in the joint, particularly synovial lining cells, resulting in initiation of what is called cell signaling or cell transduction. The terms are herein used interchangeably. As the signaling process develops, other events occur, including the activation of protein kinase C, changes in intercellular communications, and alteration of protein expression by the cells. If these processes are not regulated properly they eventually lead to osteoarthritis, which is characterized by symptoms that include pain, inflammation, abnormal neovascularization, bone and cartilage erosion, loss of function, and, ultimately, degeneration of the affected joint.

Entry of certain ions, particularly calcium and sodium ions, has been found to be critically important to the ability of the cells to secrete MMPs. As previously described, MMPs are believed to be primarily responsible for the destruction of joint cartilage that leads to joint pain associated with osteoarthritis. It is generally believed that the most important factor responsible for secretion of MMPs is interleukin-1 (IL-1). See, "Biochemistry and Metabolism of Articular Cartilage in Osteoarthritis", H. J. Mankin and K. D. Brant, supra, which is incorporated herein by reference.

The specific MMPs whose levels in joint fluid are regulated by IL-1, and whose dysregulation mediates the development of osteoarthritis, include MMP-1, also known as collagenase-1; MMP-2, also known as gelatinase A; MMP-3, also known as stromelysin-1; MMP-8, also known as collagenase-2; and MMP-13, also known as collagenase-3. The levels of MMP activity produced by synovial tissue from patients having osteoarthritis is greater than the corresponding level obtained from patients who do not have arthritis (see "Increased Intercellular Communication through Gap Junctions May Contribute to Progression of Osteoarthritis", A. A. Marino, D. D. Waddell, O. V. Kolomytkin, W. D. Meek., R. Wolf, K. K. Sadasivan, and J. A. Albright; *Clinical Orthopaedics & Related Research* 422:224-232 (2004), which is incorporated herein by reference.

Ion-channel regulators, particularly calcium-channel regulators such as verapamil and nifedipine, have been found to be capable of interfering with the effect of IL-1 on synovial cells (see "Interleukin 1β Switches Electrophysiological States of Synovial Fibroblasts"; O. V. Kolomytkin, A. A. Marino, K. K. Sadasivan, R. E. Wolf, and J. A. Albright, *American Journal of Physiology,* 273 (Regulatory Integrative Comp. Physiol. 42):R1822-R1828 (1997), which is incorporated herein by reference. It is believed, without being bound by theory, that the mechanism responsible for the beneficial effects of treating osteoarthritis with ion-channel regulators in accordance with the present invention involves their ability to antagonize the proinflammatory effect of IL-1, which if unchecked, leads to elevated levels of MMPs (which, in turn, leads to the chronic inflammation, cartilage destruction, pain and loss of joint mobility associated with osteoarthritis).

The ability to regulate or block the signaling pathway at the level of transmembrane ion current (including, but not limited to, transmembrane calcium ion current) via administration of ion-channel regulators is believed to have clinical benefits. For example, by affecting the entry of calcium ions into the affected synovial cells, the calcium signaling pathway is disrupted, preventing the intracellular events that culminate in inflammation and cartilage destruction.

As previously mentioned, ion-channel regulators may sometimes be referred to in the art as ion-channel blockers or ion-channel activators, depending on their effect on ion flow. Although these terms may refer to the same chemical agents, the terminology "ion-channel regulators" is believed to be more accurate in the context of the present invention. Ions passing through channels can turn on processes (manufacturing MMPs, for example), but these processes are always normal processes in the sense that the reason the ion channels evolved in the first place was to facilitate the process. The pathology relates to the level of regulation; that is, osteoarthritis develops when an inappropriate amount of ions pass through a channel. So, it may be said that the present invention treats osteoarthritis by blocking these channels, which amounts to allowing fewer ions to pass through the membrane, so that the situation is closer to normal. However, the coin has another side. It is not always the case that few ions equal normal and many ions equal abnormal; sometimes, many ions equal normal, and few ions equal abnormal. In this case, the present invention would not treat osteoarthritis by "blocking" the ion channel, but by "stimulating" it. Hence, the term "ion-channel regulator" is intended to include chemical agents that perform both functions.

Ion-channel regulators are commonly used for treating a variety of cardiac conditions, including atrial fibrillation, supraventricular tachycardias, hypertrophic cardiomyopathy and hypertension, as well as migraine headaches, the prevention of brain damage, and other disorders. These chemical agents are well-known to those skilled in the medical arts and it is contemplated that all known and future discovered ion-channel regulators will be useful in the present invention.

Specific examples of ion-channel regulators include, but are not limited to, calcium-channel regulators, sodium-channel regulators, potassium-channel regulators, chloride-channel regulators, cation-channel regulators, anion-channel regulators, connexon-channel regulators and non-selective ion-channel regulators, as well as specific antibodies against the channels. As the name implies, calcium-, sodium-, potassium-, chloride-, cation- and anion-channel regulators respectively regulate the movement of calcium ions, sodium ions, potassium ions, chloride ions, anions and cations through ion channels in the membranes of cells. Non-selective ion channels are ion channels that allow any combination of anions and cations to pass through the membranes of cells, and non-selective ion-channel regulators regulate the movement of those ions. Connexon-channel regulators regulate the movement of ions through connexons. Connexons are a class of ion channels consisting of the protein connexin 43, known to be present in synovial tissue and to occur in increased amounts in arthritic joints. It is believed that all types of ions with a molecular mass less than 300 are able to pass through connexons. The amino acid sequence of connexin 43 is listed at the Universal Protein Resource, where it is identified as P17302. A "specific antibody against the channel" means an antibody against an antigenic determinant of the ion-channel protein that is capable of blocking the function of the ion channel when the antibody binds to the antigenic determinant.

Representative examples of calcium-channel regulators include amlodipine, bepridil, diltiazem hypochloride, felodipine, gallopamil, isradipine, nicardipine, nifedipine, nimodipine, nitrendipine, verapamil, and mixtures thereof, as well as specific antibodies against the channels. Representative examples of sodium channel regulators include quinidine, encainide, mexitil, disopyramide, procainamide, tetrodotoxin, and mixtures thereof, as well as specific antibodies against the channels. Representative examples of potassium channel regulators include tedisamil, glibenclamide, dofetilide, amiodarone, azimilide, tolbutamide, propranolol, and mixtures thereof, as well as specific antibodies against the channels. Representative examples of chloride channel regulators include 5-Nitro-2-(3-phenylpropylamino)benzoic acid, chlorotoxin, picrotoxin, and 9-Anthracenecarboxylic acid and mixtures thereof, as well as specific antibodies against the channels. A very extensive listing of calcium- and sodium-channel regulators that may be suitable for the present invention is found in previously-cited Mak, U.S. Pat. No. 6,190,691, which is incorporated herein by reference.

Representative examples of connexon-channel regulators include lindane, octanol, 18α-glycyrrhetinic acid, calcium-ion concentration, pH, mimetic peptides, and certain antibodies. It is known that certain mimetic peptides can be used to block connexons and therefore may be suitable as connexon channel regulators in accordance with the present invention. For example, the synthetic tridecapeptide VCYDKSF-PISHVR (residue numbers 63-75), and the undecapeptide SRPTEKTIFII (residue numbers 204-214) are able to block connexin 43, as described in Leybaert, L., Braet, K., Vandamme, W., Cabooter, L., Martin, P. E. M. and Evans, W. H., "Connexin channels, connexin mimetic peptides and ATP release". Cell Commun. Adhesion. 10:251-257, 2003. Mimetic peptides consisting of 2 or more amino acids can similarly be formed employing any portion of the amino acid sequence of connexin 43, and the peptides will be effective, some more than others, in regulating the movement of ions through the connexon. Peptides that consist of amino acids located in the transmembrane or extracellular domains of connexin 43 will be particularly effective connexon channel regulators.

It is also anticipated that the connexon can be regulated by antibodies directed against the transmembrane or extracellular domains of the connexon. In this case, the synthetic peptides may be injected into animals for the purpose of eliciting an immune response consisting of antibodies against epitopes located on the peptides. Suitable procedures for obtaining and purifying the antibodies are described in Harlow, E. and Lane, D., "Antibodies: A Laboratory Manual." Woodbury, N.Y.: Cold Spring Harbor Laboratory Press, 1988.

In one embodiment of the present invention, a method for treating osteoarthritis comprises directly administering to the joint an effective amount of at least one ion-channel regulator. Administering the ion-channel regulator is preferably accomplished by direct (intraarticular) injection of a composition comprising at least one ion-channel regulator into an arthritic joint. Intraarticular injection differs from other methods of administering ion-channel regulators in that it allows biologically sufficient concentrations of ion-channel regulator to be applied to the affected synovial tissue without the risk of producing the undesirable side-effects that can occur as the result of the higher concentrations of ion-channel regulator required by other administration techniques. Injection techniques are known to those skilled in the art. For example, a useful description for injecting the knee joint is given in "Viscosupplementation Under Fluoroscopic Control," D. Waddell, D. Estey, D. C. Bricker, and A. Marsala, American Journal of Medicine in Sports, 4:237-241 and 249, 2001, which is incorporated by reference herein.

In one embodiment of the invention, an effective amount of one or more ion-channel regulators is administered to an osteoarthritic joint in a pharmaceutically acceptable composition. An "effective amount" is an amount that is sufficient to reduce any or all of the symptoms of osteoarthritis in the treated joint, such as inflammation, pain, stiffness and/or loss of function, without producing any of the undesirable side effects resulting from an overdose of ion-channel regulator, such as tissue death or injury, joint swelling, etc. What is an effective amount will vary depending on the ion channel, the method used for administration and the joint being treated. In some embodiments, a combination of ion-channel regulators, e.g. a calcium-channel regulator and a sodium-channel regulator, may be effective.

An effective amount of ion-channel regulator for treating osteoarthritis in accordance with the present invention using intraarticular injection may be in the range of 0.00001-2.0 mg, preferably dissolved or suspended in physiological saline or other vehicle appropriate for injection into the body. Preferred compositions comprise one or more ion-channel regulators at a total concentration of 0.00001-2.0 mg/mL. Typically 1-4 mL of the composition may be injected into the joint at one time. Administration of a total dose of more than 2.0 mg of ion-channel regulator to a joint by intraarticular injection has been found on the basis of appropriate studies of synovial tissue to be likely to produce undesirable side effects resulting from the toxic effect of the ion-channel regulator on joint tissue at that level. An effective amount of ion-channel regulator used in the present invention is an order of magnitude less than the amount of (+)-verapamil that is taught in the prior art as being effective for the treatment of rheumatoid arthritis by intraarticular injection. See, for example, Mak U.S. Pat. No. 6,190,691, col. 83, lines 35-54. As one specific example of the present invention, an effective amount of verapamil may be 0.02-0.5 mg when directly injected into an adult knee joint.

In another embodiment of the invention, one or more ion-channel regulators may be administered in combination with one or more other osteoarthritis treatment agents, either in separate compositions or in the same composition. Preferably, the other osteoarthritis treatment agent is in the form of an injectable composition, i.e. a composition that is suitable for being injected directly into the affected joint (intraarticular injection). The treatment method of the present invention can readily be customized to the individual patient's needs, and may be used instead of or in conjunction with other treatment modalities including but not limited to physical therapy, treatments that provide localized pain relief (heat, massage, application of liniments, etc.), and with other medications that help reduce disability, relieve pain, and improve the patient's quality of life.

Accordingly, examples of treatments contemplated by the present invention include an intraarticular injection of a composition including one or more ion-channel regulators followed by another intraarticular injection of another osteoarthritis treatment agent, e.g. a viscosupplement, steroid or other injectable osteoarthritis treatment agent; an intraarticular injection of an ion-channel regulator composition followed by oral or intravenous administration of another osteoarthritis treatment agent such as a non-steroidal anti-inflammatory drug; an intraarticular injection of a single composition comprising at least one ion-channel regulator and at least one viscosupplement, steroid or other injectable osteoarthritis treatment agent; and so forth.

A treatment composition according to one embodiment of the invention comprises one or more ion-channel regulator(s) and one or more other osteoarthritis treatment agent(s). The individual concentrations of the ion-channel regulator(s) and the other osteoarthritis treatment agent(s) are sufficient to provide an effective amount of each ingredient to the affected joint. Preferably, the composition comprises ion-channel regulator(s) at a concentration of 0.00001-2.0 mg/mL and other osteoarthritis treatment agent(s) at a concentration of 0.01-25 mg/mL.

In one embodiment, the composition is suitable for intraarticular injection in accordance with the method of the present invention, and both the ion-channel regulator and other osteoarthritis treatment agent are "injectable". As used herein, the term "injectable" means any osteoarthritis treatment agent that is in a form suitable for intraarticular injection. In one embodiment, the injectable other osteoarthritis treatment agents may comprise at lease one corticosteroid such as a glucocorticoid. As one specific non-limiting example, the composition of the present invention may comprise 1-25 mg/mL of the injectable steroid osteoarthritis treatment agent methylprednisolone acetate.

In another embodiment, the injectable other osteoarthritis treatment agent may comprise at least one viscosupplement. As used herein and in the art, the term "viscosupplement" refers to any substance that is used to restore and/or increase the cushioning and lubrication of arthritic synovial fluid by intraarticular injection. Preferred viscosupplements include hylan, hyaluronic acid and other hyaluronan (sodium hyaluronate) compounds, which are natural complex sugars of the glycosaminoglycan family. Hyaluronan, in particular, is a long-chain polymer containing repeating disaccharide units of Na-glucoronate-N-acetylglucosamine. By way of example, commercially available hyaluronan viscosupplements include Synvisc®, Hyalgan®, Supartz®, and Orthovisc®. As one specific non-limiting example, the composition of the present invention may comprise 1-15 mg/mL of a hyaluronon compound.

Other osteoarthritis treatment agents comprising the composition of the present invention may also include those used in any modality of arthritis treatment, such as oral administration, intravenous administration, etc. Examples of other osteoarthritis treatment agents include, without limitation, non-steroidal anti-inflammatory drugs (NSAIDS) such as ibuprofen, naproxen, and COX-2 inhibitors; analgesics such as aspirin and acetaminophen; glycans, including glucosamines, e.g. glucosamine sulfate and glucosamine hydrochloride; and proteoglycans, such as chondroitin compounds, as well as various other known narcotics, steroids, antibiotics, immunomodulators, penicillamine, and the like.

The compositions of the present invention may also contain other materials such as fillers, stabilizers, coatings, coloring agents, preservatives, fragrances, and other additives known in the art. The compositions may be in liquid or gel form and may be provided in time-release formulations.

The present invention may be illustrated by the following non-limiting examples:

Example 1

Patient M. L. is a 57-year-old female with osteoarthritis of the knee joint (grade IV on the Kellgren-Lawrence scale). An assessment of pain and function of the joint was made immediately prior to treatment, and at various times after treatment, using the visual analog scale (VAS) for pain, and the Western Ontario and McMaster Universities (WOMAC) osteoarthritis index, which assesses pain, function and stiffness in arthritic joints. A more detailed description of the nature and use of these clinical endpoints is given in "Clinical Development Programs for Drugs, Devices, and Biological Products Intended for the Treatment of Osteoarthritis, U.S. Dept. of Health and Human Services, Food and Drug Administration, July 1999", which is incorporated by reference herein.

Immediately after the initial VAS and WOMAC measurements were made, the patient's right knee was injected with 1 mL of saline containing 0.2 mg of the calcium-channel regulator verapamil using the following basic injection procedure:

The patient is seated in a standard dental chair, with the knee flexed between 30-40 degrees. The knee is prepared with a sterile prep of betadine. Ethyl chloride spray provides skin anesthesia for the injection of 1% plain Xylocaine, which is injected into the skin and subcutaneous tissue. Precaution is taken not to inject any fluid into the knee. The patient is cautioned that although the majority of pain will be obviated, there will be some pain as the needle passes through the synovial lining. After enough time has elapsed to achieve effective local anesthesia, it is often useful to activate a fluoroscopy unit in the lateral position to obtain a view of the patella and contact zone of the femoral condyle with the tibial plateau. The point of insertion for the 21-gauge injection needle is then chosen utilizing the lateral view of the knee and referencing the point of a standard anterolateral arthroscopy portal. The injection site is proximal to the normal portal site by some 1 to 1½ centimeters. Using this as a guide, the needle is advanced inwardly to the intraarticular space just at the anterior contact point of the femoral condyle and the tibial plateau. At this point, free injection of verapamil is allowed without injecting the soft tissues. The above procedure is described in more detail in the aforementioned journal entitled "Viscosupplementation Under Fluoroscopic Control," cited supra.

Table 1 below summarizes the VAS and WOMAC scores obtained before and at several time points after the injection.

TABLE 1

| | Arthritis Scores of Patient M. L. | | |
| --- | --- | --- | --- |
| Time | Physician VAS | Patient VAS | WOMAC |
| Prior to injection | 72 | 67 | 57 |
| 1 week after injection | 44 | 43 | 47 |
| 2 weeks after injection | 20 | 25 | 38.5 |
| 3 weeks after injection | 20 | 33 | 46 |
| 8 weeks after injection | 20 | 33 | 34 |
| 12 weeks after injection | 20 | 28 | 41 |
| 16 weeks after injection | 28 | 34 | 33 |
| 20 weeks after injection | 15 | 27 | 37 |

As shown in Table 1, immediately before treatment, the patient had a physician VAS score of 72, a patient VAS score of 67, and a WOMAC score of 57. One week after injection, the patient's pain had decreased markedly, as indicated by the reduced VAS scores of 44 and 43, and the patient's overall function had improved, as evidenced by the decrease in WOMAC score to 47. The patient was followed periodically for up to 20 weeks following the injection, and it was found that the reduction in pain and improvement in function continued to be observed.

Example 2

Patient O. B. is a 73-year-old male who suffered from osteoarthritis in the left knee (grade IV on the Kellgren-Lawrence scale). As can be seen in Table 2 below, prior to treatment, the patient had a physician VAS score of 50, a patient VAS score of 46 and a WOMAC score of 30. After the patient's left knee was injected with 1 mL of saline containing 0.2 mg of verapamil using the same basic procedure described in Example 1, both VAS scores and the patient's WOMAC score improved significantly. Table 2 below summarizes those results:

TABLE 2

| | Arthritis Scores of Patient O. B. | | |
|---|---|---|---|
| Time | Physician VAS | Patient VAS | WOMAC |
| Prior to injection | 50 | 46 | 30 |
| 1 week after injection | 12 | 28 | 12 |
| 2 weeks after injection | 11 | 25 | 10 |
| 3 weeks after injection | 10 | 10 | 6 |
| 8 weeks after injection | 12 | 17 | 4 |

Example 3

Patient R. R. is a 41-year-old male suffering from osteoarthritis in the left knee joint (grade II on the Kellgren-Lawrence scale). Prior to treatment, the patient's chief complaint was pain, as evidenced by a patient VAS of 55. Following treatment with 0.5 mg of verapamil in 1 mL of saline employing the same basic injection procedure as set forth in Example 1, the patient's pain decreased and remained low throughout the period for which data was collected. Table 3 below summarizes those results:

TABLE 3

| | Arthritis Scores of Patient R. R. | | |
|---|---|---|---|
| Time | Physician VAS | Patient VAS | WOMAC |
| Prior to injection | 35 | 55 | 17 |
| 1 week after injection | 10 | 12 | 8 |
| 2 weeks after injection | 6 | 26 | 7 |
| 3 weeks after injection | 10 | 16 | 6 |
| 8 weeks after injection | 11 | 20 | 6 |
| 12 weeks after injection | 12 | 20 | 6 |
| 16 weeks after injection | 10 | 10 | 6 |

Example 4

Patient A. W. is a 56-year-old female who initially had physician and patient VAS scores of 50 and 59, respectively and also had limited joint function as indicated by a WOMAC of 43. Following treatment with 0.2 mg of verapamil in 1 mL of saline employing the same basic injection procedure as set forth in Example 1, her clinical condition improved markedly, as shown in Table 4.

TABLE 4

| | Arthritis Scores of Patient A. W. | | |
|---|---|---|---|
| Time | Physician VAS | Patient VAS | WOMAC |
| Prior to injection | 50 | 59 | 43 |
| 1 week after injection | 0 | 5 | 12 |
| 2 weeks after injection | 7 | 3 | 7 |
| 3 weeks after injection | 8 | 6 | 13 |
| 8 weeks after injection | 2 | 2 | 15 |

The destructive action of MMPs and the role of potentially useful agents to block this destructive activity can be studied in a model system involving synovial tissue obtained from knee joints, a pro-inflammatory agent which causes the tissue to secrete MMPs, and an agent whose effectiveness in reducing MMP production is to be assessed. A procedure suitable for performing this assay is described in Kolomytkin, O. V., Marino, A. A., Waddell, D. D., Mathis, J. M., Wolf, R. E., Sadasivan, K. K. & Albright, J. A., "IL-1β-induced production of metalloproteinases by synovial cells depends on gap-junction conductance during the early stage of signal transduction." Am. J. Physiol: Cell Physiol. 282:C1254-C1260, 2002. which is incorporated by reference herein and should be consulted for more detail.

The following results of tests using the above-described procedure confirm that the administration of an ion-channel regulator to synovial tissue in accordance with the present invention significantly reduces the production and secretion of MMPs by the treated synovial tissue. As previously stated, this reduction in MMPs is believed to lead to the reduction in pain and improvement in function achieved by the method of the present invention, e.g. as demonstrated in Examples 1-4 above.

Example 5

When approximately 20 mg of synovial tissue was obtained from a 78-year-old female with osteoarthritis (grade IV, Kellgren-Lawrence scale), it was found using the above-described procedure that the amount of MMPs produced under standard incubation conditions was reduced 60% when the calcium-channel regulator verapamil was applied at a concentration of 0.005 mg/mL, total volume, 1 mL; and the MMPs were reduced 63% when the concentration of verapamil was increased to 0.05 mg/mL in the same volume. In another patient, a 61-year-old female, the MMP activity was decreased by 63% in the presence of a verapamil concentration of 0.005 mg/mL and by 77% in the presence of verapamil at a concentration of 0.05 mg/mL; both with total volume of 1 mL. Similar results were found using synovial tissue from a 69-year-old male and a 70-year-old female, both of whom had osteoarthritis (grade IV, Kellgren-Lawrence scale).

Example 6

Experiments were performed using the procedure described above, but using the calcium-channel regulator nifedipine instead of verapamil. It was found that the amount of MMPs produced under standard conditions by approximately 20 mg of synovial tissue obtained from a 73-year-old female with osteoarthritis (Grade IV, Kellgren-Lawrence) was reduced by 69% in the presence of a 0.015 mg/mL of nifedipine, total volume, 1 mL; and the MMP activity was reduced by 76% at a nifedipine concentration of 0.03 mg/mL, total volume, 1 mL. When the assay was repeated using synovial tissue from a 59-year-old female with osteoarthritis (grade IV, Kellgren-Lawrence scale), the MMP activity produced by the tissue under standard conditions was reduced by 64% and 71% when the tissue was exposed to 0.015 mg/mL nifedipine and 0.03 mg/mL nifedipine, respectively. Similar results were obtained using the synovial tissue of a 50-year-old male and a 68-year-old female, both of whom had osteoarthritis (grade IV, Kellgren-Lawrence scale).

Example 7

Experiments were performed using the procedure described above, but using the sodium-channel regulator procainamide instead of a calcium-channel regulator. It was found that the amount of MMP produced under standard conditions by approximately 20 mg of synovial tissue obtained from a 77-year-old male with osteoarthritis (Grade IV, Kellgren-Lawrence) was reduced by 67% when the tissue was treated with 0.01 mg/mL; total volume, 1 mL.

Example 8

Experiments were performed using the procedures described above, but using the sodium-channel regulator tetrodotoxin. It was found that the amount of MMP produced under standard conditions by approximately 20 mg of synovial tissue obtained from a 64-year-old male with osteoarthritis (Grade IV, Kellgren-Lawrence) was reduced by 100% when the tissue was treated with 0.00002 mg/mL; total volume, 1 mL.

The trypan blue exclusion test is commonly used to evaluate whether cells are alive or dead. The test consists of adding an appropriate amount of trypan blue dye to the environment of the cells. Cells are able to exclude the dye if they are healthy, but if they are injured or dead, the dye enters the cell and stains it blue. By means of the trypan blue exclusion test, as described in Example 9 below, it was found that ion-channel regulators produce harmful and lethal effects on cells when used to treat osteoarthritis at concentrations taught by the prior art to treat rheumatoid arthritis.

Example 9

Approximately 20 mg of synovial tissue from a human knee joint was exposed to 10 mg/mL of the ion-channel regulator verapamil (1 mL total volume) and assessed using the trypan blue dye exclusion test. It was found that the synovial lining cells in the tissue were killed. Some cell death occurred after exposure for several hours, and all of the cells in the tissue were killed following exposure for 12-16 hours. Similar tests were performed on additional samples of human synovial tissue using various concentrations of different ion-channel regulators.

By means of the above-described tests, it was discovered that the concentration of verapamil, nifedipine, procainamide, and other ion-channel regulators used in compositions of the present invention must be no greater than 2.0 mg/mL, and that the total dose of the ion-channel blocker must be no greater than 2.0 mg. The markedly lower concentration and dosage used in the practice of the present invention have the further significant advantage of completely avoiding systemic side-effects which may be anticipated to occur at the concentrations and doses described in the prior art, e.g. intraarticular injection of 20-40 mg of verapamil in a 10 mg/mL aqueous solution as described in Mak U.S. Pat. No. 6,190,691 for treatment of rheumatoid arthritis.

The foregoing description is considered as illustrative only of the principles of the invention. Further, since numerous modifications and changes will readily occur to those skilled in the art, it is not desired to limit the invention to the exact details shown and described herein, and accordingly, all suitable modifications and equivalents may be resorted to, falling within the scope of the invention. Thus, it will be apparent to those skilled in the art that many changes and substitutions can be made to the preferred embodiments herein described without departing from the spirit and scope of the present invention as defined by the appended claims.

What is claimed is:

1. A method of treating osteoarthritis in a patient in need thereof, comprising:
   administering in a single dose, a pharmaceutically acceptable composition comprising 0.02 to 0.5 mg of a calcium ion-channel regulator into an intraarticular space of a joint of the patient; wherein about 12 weeks after the single dose administration the patient has substantial improvement in the joint function.

2. The method of claim 1, wherein the substantial improvement is measured by a WOMAC score.

3. The method of claim 1, wherein after about 16 weeks the patient has substantial improvement in the joint function.

4. The method of claim 1, wherein after about 20 weeks the patient has substantial improvement in the joint function.

5. The method of claim 1, wherein 1 to 4 mL of the composition is administered.

6. The method of claim 1, wherein the calcium-channel regulator is verapamil, nifedipine, or diltiazem.

* * * * *